United States Patent [19]

Lampert

[11] 4,207,677
[45] Jun. 17, 1980

[54] DENTAL MODEL ARTICULATOR

[75] Inventor: Barry Lampert, Huntington, N.Y.

[73] Assignee: Rab Tec Products Corporation, Freeport, N.Y.

[21] Appl. No.: 953,442

[22] Filed: Oct. 23, 1978

[51] Int. Cl.² ............................................. A61C 11/00
[52] U.S. Cl. ........................................ 433/60; 433/54
[58] Field of Search ............................................. 32/32

[56] References Cited

U.S. PATENT DOCUMENTS

| | | | |
|---|---|---|---|
| 2,556,639 | 6/1951 | Wimberly | 32/32 |
| 3,466,750 | 9/1969 | Timberlake et al. | 32/32 |
| 3,727,311 | 4/1973 | Schoonebock | 32/32 |
| 3,823,476 | 7/1974 | Hudson | 32/32 |

Primary Examiner—Robert Peshock
Attorney, Agent, or Firm—Stephen E. Feldman; Marvin Feldman

[57] ABSTRACT

The upper and lower jaw members and intermediate connecting member of a dental model articulator are molded from suitable plastic as an integral unitary whole; with the jaw members spaced from each other, by the intermediate connecting member, a distance comensurate with the dental models to be mounted on the articulator, and so that the upper jaw member articulates with respect to the intermediate member and lower jaw member to facilitate relative positioning of, and the performing of work on, the dental models. An over-center toggle-type-hinge is integrally molded between the upper jaw member and the intermediate connecting member to provide for articulation of the upper jaw member. Each jaw member has formed therein a centrally disposed slot with shoulders extending from each wall thereof so as to leave a narrow passage or slit formed to receive a rib of a dental model mounting plate and thus to facilitate positioning of the plate, and a dental model when carried thereby on its respective jaw member of the articulator. The rib of the dental model mounting plate is formed in a modified "T" shaped configuration to enter into the slit between the shoulders while at the same time snugly positioning such shoulders between the arm of the "T" and the corresponding surface of the mounting plate. Suitable apertures and ribs are formed in the jaw and connecting members to facilitate its production while at the same time providing a required degree of flexible rigidity.

9 Claims, 6 Drawing Figures

DENTAL MODEL ARTICULATOR

BACKGROUND OF THE INVENTION—FIELD OF APPLICATION

This invention relates to the mounting of dental models; and more particularly to dental articulators for mounting dental models.

BACKGROUND OF THE INVENTION—DESCRIPTION OF THE PRIOR ART

The skilled dental artisan, when fabricating, repairing or otherwise working on artificial teeth, or dentures as they are more commonly known, usually utilizes a dental model of his patient's upper and lower gums and/or teeth. Clearly it is easier and much more efficient for the dental artisan to work with a dental model of his patient rather then directly in the patient's mouth; except for final fittings and adjustments.

In working with such dental models it has become commonplace to utilize dental model articulators to hold and position the dental models in at least two possible positions. One such position is one where the dentures (or gums) are disposed as though positioned in the patient's mouth when normally closed. Another position is one where the dentures (or gums) are seperated so that the artisan can perform the needed work.

A significant number of articulators available today are relatively complex in construction and use. As such they are cumbersome to use and affect the cost of preparing and servicing dentures. In an effort to minimize the detrimental costs of allocating a single such articulator to each dental model set some prior art devices have been designed to permit separation and replacement of dental models on a single articulator; and thus the use of one such articulator with a number of different dental models. Some of these prior art articulators, such as those shown in U.S. Pat. No. 2,365,475 issued on Dec. 19, 1944 to I. Klein for Dental Mounting Service and in U.S. Pat. No. 2,629,929 issued on Mar. 3, 1953 to C. Levine et al., for Mounting For Artificial dentures, require the use of plaster moulding to secure the model plate to the articulator, and a relatively complex system of aligning apertures, lugs, threaded securing elements and the use of securing pins that have to be inserted through small holes in tight places. All of this is tedious and cumbersome and any savings which might result from the ability to utilize a single articulator with a number of models is quickly disipated by the extra labor entailed in positioning the models on the articulator.

Other prior art approaches to the problem utilize a mounting plate which is secured to the dental model by various and sundry different aligning and securing means. Such devices are exemplified by the showings in U.S. Pat. No. 3,123,914 issued on Mar. 10, 1964 to A. J. De Pietro for Mounting Plate; U.S. Pat. No. 3,750,289 issued on Aug. 7, 1973 to Niles F. GuiChet for Centric Relating Device; U.S. Pat. No. 3,965,576 issued on June 29, 1976 to Melbourne D. Eveland for Dental aparatus and Method; and U.S. Pat. No. 3,908,271 issued on Sept. 30, 1975 to Henry J. Derda for Dental Articulator. All of these still require locating pins and apertures with their aforementioned shortcomings and dentrimental affect upon the cost of dentures.

SUMMARY OF THE INVENTION

It is therefore an object of this invention to provide a new and improved dental model articulator.

It is another object of this invention to provide a new and improved dental model articulator which is relatively inexpensive to fabricate.

It is yet another object of this invention to provide a new and improved dental model articulator which is fabricated out of relatively inexpensive materials.

It is yet another object of this invention to provide a new and improver dental model articulator which is fabricated as a unitary and integral device.

It is still a further object of this invention to provide a new and improved dental model articulator which is molded as an integral and unitary device from plastic.

It is yet still a further object of this invention to provide a new and improved dental model articulator which is molded as an integral and unitary device and so that one of the dental model mounting members can articulate between at least two different positions.

This invention involves dental model articulators; and contemplates forming such articulators with the upper and lower jaw members and their interconnecting member all formed as an integral and unitary whole and with a built in over-center-toggle type hinge so that one of said jaw members is movable with respect to the other between at least two distinct positions. Each jaw member is additionally formed to removably receive a dental model mounting plate.

Other objects, features, and advantages of the invention in its details of construction and arrangement of parts will be seen from the above, from the following description of the preferred embodiment when considered with the drawing and from the appended claims.

BRIEF DESCRIPTION OF THE PREFERRED EMBODIMENT

For convenience the invention will be described as applied to a dental articulator integrally and unitarily molded from vinyl plastic, with reinforcing ribs formed about the underside of the lower jaw member and the front face of the vertically disposed member connecting the lower jaw member to the upper jaw member, with a relatively large material saving opening formed through said connecting member, with each jaw member formed with a pair of longitudinally extending grooves within each of which are two apertures, and with each jaw member including a slot having shoulders extending from the side walls thereof towards each other to form a slit for receiving a modified "T" shaped rib of a dental model mounting plate. It should be understood, nevertheless that without departing from the scope of this invention; thst other suitable plastics may be used; that the reinforcing ribs may be formed on other parts of the device or eliminated in favor of alternate reinforcing means; that the large material saving opening may be formed of alternate configurations, as multiple openings or it may be eliminated altogether; that the grooves may be otherwise formed or eliminated completely; the the dual apertures in the grooves may be replaced by a single aperture or no aperture at all; and that the slot and slit configuration may be of alternative configurations depending upon the mating dental model plate attaching structure.

Figure 1:
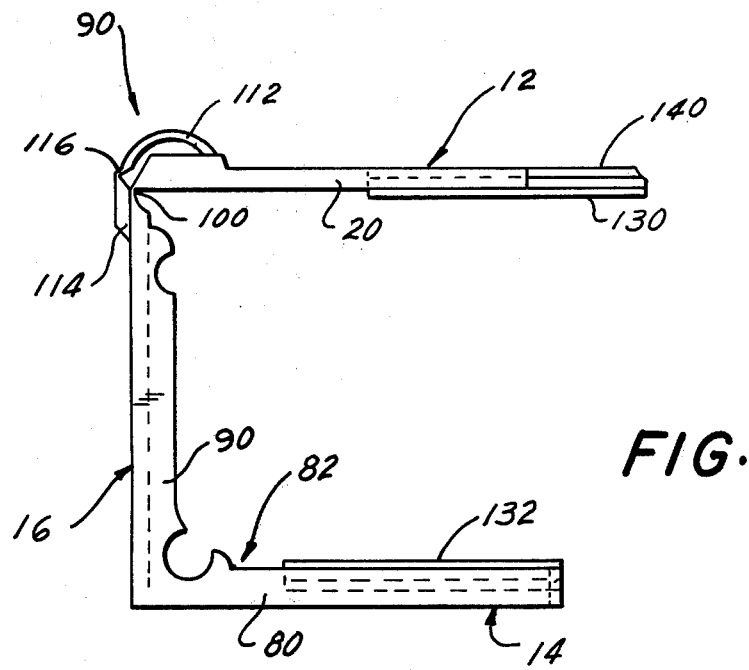
FIG. 1 is a side elevational view of a dental articulator incorporating the instant invention.
Figure 2:
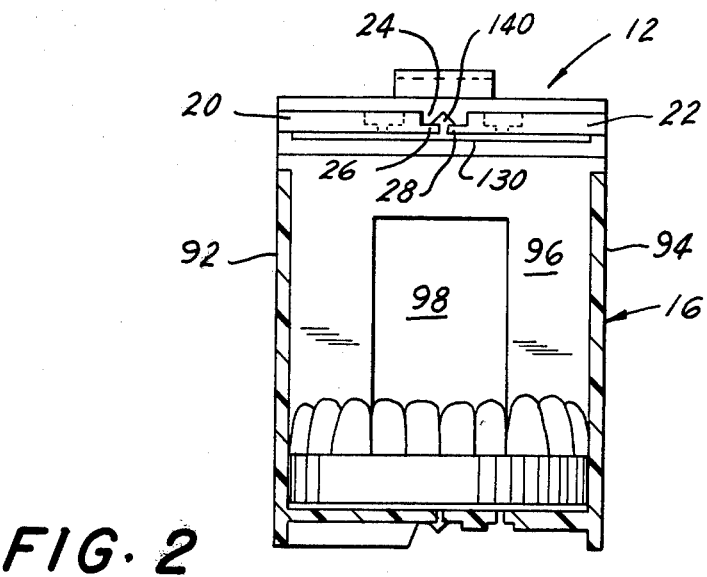
FIG. 2 is a front elevational view of the dental articulator of FIG. 1 with a dental model carried by a model mounting plate in position on the lower bow thereof.
Figure 3:
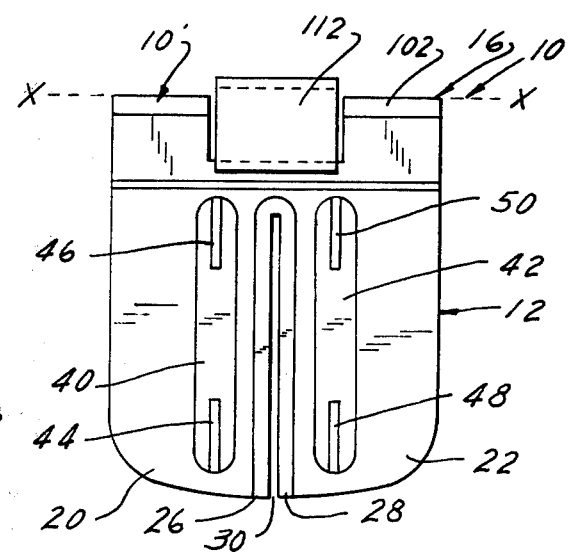
FIG. 3 is a top view of the dental articulator of FIG. 1.

With reference to FIGS. 1, 2 and 3 there is generally shown at 10 a dental model articulator including an upper jaw member 12, a lower jaw member 14, and an intermediate connecting member 16. Member 12, 14, and 16 are integrally and unitarily molded of a suitable plastic, such as vinyl plastic; and sized to accomodate the size of dental models that are to be mounted to upper jaw member 12 and lower jaw member 14 as will be hereinafter explained.

Upper jaw member 12 is formed with a left side bow member 20, and a right side bow member 22 separated by a slot 24 (FIG. 2). A pair of shoulders 26, 28 (FIGS. 2 and 3) extend from the side walls of slot 24 towards each other but so as to leave a narrow passage or slit 30 therebetween for purposes to be hereinafter explained. Longitudinal grooves 40, 42 are formed into the top surfaces of bows 20, 22 respectively. A pair of apertures 44,46 extend from the bottom surface of groove 40 through bow member 20; while a similar pair of apertures 48, 50 extend from the bottom surface of groove 42 through bow member 22.

Lower jaw member 14 is also formed with a left side bow member 60, and a right side bow member 62 seperated by a slot 64. A pair of shoulders 66, 68 (FIG. 2) extend from the side walls of slot 64 towards each other but so as to leave a narrow passage or slit similar to slit 30 of upper jaw member 12 and for the same purpose. Longitudinal grooves 74 are formed in left bow member 60 and right bow member 62 respectively and in a manner and configuration similar to grooves 40, 42. A pair of apertures 76 extend from the bottom surfaces of grooves 74 through bow members 60 and 62 in a manner and configuration similar to apertures 44, 46, 48, and 50.

Lower jaw member 14 includes a reinforcing rib 80 formed about the periphery thereof to add strength thereto while permitting some degree of flexing of bow members 60, 62 with respect to each other and with respect to a rear portion 82 of lower jaw member 14.

Intermediate connecting member 16 meets rear portion 82 of lower jaw member 14 at substantially a right angle; and extends upwardly therefrom until it connects with upper jaw member 12 by means of an articulating over-center toggle-type-hinge 90 formed integral between upper jaw member 12 and connecting member 16 during the molding process. A left side reinforcing rib 92 and a right side reinforcing rib 94 extend forward from a facing surface 96 of connecting member 16. A large opening 98 is formed through member 16 to lighten the weight of the device while at the same time saving the expense of the material.

Hinge 90, as previously mentioned is integrally formed during the molding process and is of the over-center-toggle type. A hinge portion is formed by molding a relatively thin cross-section as at 100 and 102 so as to permit flexing therebout along an inaginary line X—X seperating the back end of upper jaw 12 and the upper end of connecting member 16. An over-center toggle 110 is formed by integrally molding a curved member 112 to upper jaw 12 and a toggle block 114 to connecting member 16 with a relatively thin hinge 116 there between.

Figure 4:
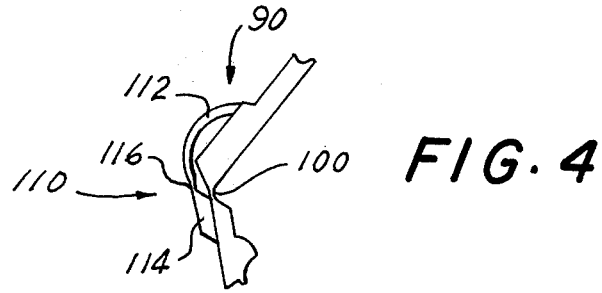
FIG. 4 is a partial detail view of the hinge portion of the dental articulator of FIG. 1 showing said hinge in its "spaced" position.

The action of over-center toggle 110 is such that upper jaw member 12 is either detented into a first or "spaced" position (FIG. 4) wherein the maximum spacing is provided between upper jaw 12 and lower jaw 14 to permit the dental artisan to work on dental models when carried thereby; or such that upper jaw 12 is biased into a position against connecting member 16 into a position wherein a dental model carried thereby is urged towards a dental model carried by lower jaw 14.

Figure 5:
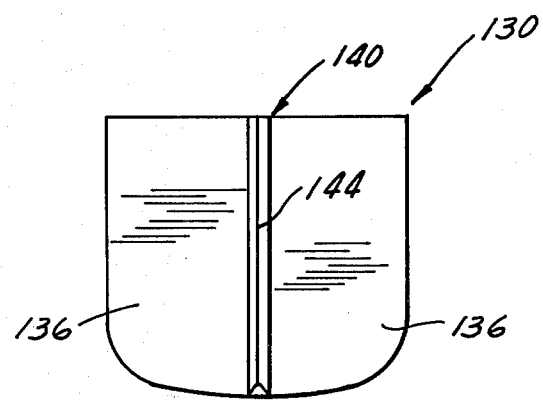
FIG. 5 is a plan view of a dental model mounting plate usable with the dental articulator of FIG. 1.
Figure 6:
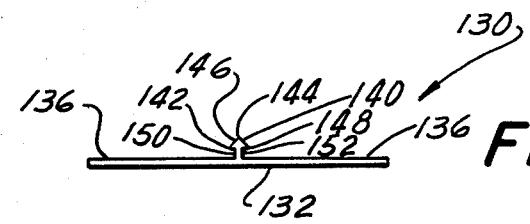
FIG. 6 is an end view of the dental model mounting plate of FIG. 5.

A dental model mounting palte 130 (FIGS. 5 and 6) formed from vinyl plastic, or other suitable material, is formed to a size approximating bow members 20, 22 of upper jaw member 12 and/or bow members 60, 62 of lower jaw member 14. A first substantially planar surface 132 (FIG. 6) of plate 130 is formed to be substantially flat and so as to be readily secured to dental model 134 (FIG. 2) by conventionally available means. A second substantially planar surface 136 of plate 130 includes an upstanding rib 140 in the form of a modified "T". Rib 130 is formed with a vertical leg 142 and a cross arm 144 which tops leg 142 and extends to both sides thereof forming shoulders 146, 148 substantially parallel to planar surface 136. As such a pair of grooves 150, 152 are formed between shoulders 146, 148 and planar surface 136. The size and configuration of grooves 150, 152 is such as will enable them to receive a corresponding shoulder 26, 28 or 66, 68 or upper jaw 12 or lower jaw 14, respectively.

In use the technician, or other user, merely slides dental model mounting plate 130 onto its respective jaw member (12 or 14). Vertical leg 142 of rib 140 of plate 130 slides into slit 20 (or the comparable slit for lower jaw 14) and shoulders 146, 148 of cross arm 144 span shoulders 26, 28 (or 66, 68) so that shoulders 26, 28 (or 66, 68) are snugly lodged in grooves 150, 152 or rib 140. Dental model 134 is either already in place on plate 130 or may thereafter be disposed securely thereon. To remove dental model 134 from articulator 10 one need merely slide plate 130 so that rib 140 seperates from slit 30.

If desired the user may leave the dental models on articulator 10 or they may use a single articulator 10 for many different model sets.

From the above description it will thus be seen that there has been provided a novel improved dental model articulator; which articulator is integrally and unitarily molded from a relatively lightweight plastic material to provide an easy to use device for positioning dental models during the fabrication, servicing and storage thereof.

It is understood that although I have shown the preferred form of my invention that various modifications may be made in the details thereof without departing from the spirit as comprehended by the following claims.

I claim:
1. A dental articulator, comprising:
   (a) a lower jaw member;
   (b) an upper jaw member;

(c) an intermediate member connecting said upper jaw member and said lower jaw member in spaced relationship one with respect to the other; and (d) articulating means operatively associated with said upper jaw member to articulate with respect to said intermediate member and said lower jaw member, said articulating means comprising detenting means comprising a toggle being disposed between the upper jaw and the intermediate member and being operatively associated with the upper jaw member for movement of the upper jaw member with respect to the intermediate member and said lower jaw member whereby the detenting means is disposed adjacent to the upper jaw member and the intermediate member.

2. The dental articulator of claim 1 wherein said upper jaw member, said lower jaw member and said intermediate member are molded as a unit from the same material.

3. The dental articulator of claim 2 wherein said upper jaw member, said lower jaw member and said intermediate member are all integrally and unitarily molded from plastic.

4. The dental articulator of claim 3 wherein said articulating means includes hinge means integrally formed between said upper jaw member and said intermediate member during the molding thereof.

5. The dental articulator of claim 4 wherein said articulating means includes dententing means integrally formed between said upper jaw member and said intermediate member during the molding thereof.

6. The dental articulator of claim 1 wherein said upper jaw member and said lower jaw member are each formed with left and right portions seperated by a slot, with shoulders extending from side walls of each slot towards each other so as to form slots therebetween.

7. The dental articulator of claim 6 including at least one dental mounting plate of a size and configuration corresponding to either said upper or said lower jaw members and formed with a modified "T" shaped rib extending from a surface of said dental mounting plate and of a size and configuration for coaction with said slit and shoulders of either said upper or said lower jaw members to facilitate disposition of said dental mounting plate thereon.

8. The dental articulator of claim 7 including a second dental mounting plate for coacting with the other one of said upper or lower jaw members.

9. The dental articulator of claim 8 including a groove formed in one surface of each of said portions of and a pair of apertures extending from the bottom of each such groove through the portions.

* * * * *